(12) United States Patent
Shirakawa et al.

(10) Patent No.: US 8,487,141 B2
(45) Date of Patent: Jul. 16, 2013

(54) METHOD FOR PRODUCING A PERFLUORO COMPOUND HAVING HYDROXYL GROUPS

(75) Inventors: Daisuke Shirakawa, Tokyo (JP); Yoshiyuki Gozu, Tokyo (JP); Yoshitomi Morisawa, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 28 days.

(21) Appl. No.: 13/038,472

(22) Filed: Mar. 2, 2011

(65) Prior Publication Data

US 2011/0152567 A1    Jun. 23, 2011

Related U.S. Application Data

(63) Continuation of application No. PCT/JP2009/065688, filed on Sep. 8, 2009.

(30) Foreign Application Priority Data

Sep. 9, 2008 (JP) ................................. 2008-230708

(51) Int. Cl.
*C07C 31/34* (2006.01)

(52) U.S. Cl.
USPC ........................................................ 568/842

(58) Field of Classification Search
None
See application file for complete search history.

(56) References Cited

U.S. PATENT DOCUMENTS

| | | | | |
|---|---|---|---|---|
| 6,509,509 B2 * | 1/2003 | Tonelli et al. | .................. | 568/606 |
| 6,573,411 B2 * | 6/2003 | Russo et al. | .................. | 568/615 |
| 7,795,375 B2 | 9/2010 | Shirakawa et al. | | |
| 2006/0252910 A1 * | 11/2006 | Shirakawa et al. | ........... | 528/401 |
| 2007/0116990 A1 | 5/2007 | Shirakawa et al. | | |
| 2008/0132664 A1 | 6/2008 | Shirakawa et al. | | |
| 2010/0240559 A1 | 9/2010 | Shirakawa | | |
| 2010/0240560 A1 | 9/2010 | Shirakawa et al. | | |

FOREIGN PATENT DOCUMENTS

| | | |
|---|---|---|
| JP | 2001-226482 | 8/2001 |
| JP | 2003-12588 | 1/2003 |
| JP | 2003-26795 | 1/2003 |
| JP | 2004-339221 | 12/2004 |
| JP | 2005/068534 | 7/2005 |
| JP | 2007-186454 | 7/2007 |
| JP | 2008-1632 | * 1/2008 |

OTHER PUBLICATIONS

Machine Translation of 2008-1632.*
International Search Report issued Dec. 22, 2009 in PCT/JP09/065688 filed Dec. 9, 2009.
U.S. Appl. No. 13/440,117, filed Apr. 5, 2012, Shirakawa, et al.

* cited by examiner

*Primary Examiner* — Karl J Puttlitz

(74) *Attorney, Agent, or Firm* — Oblon, Spivak, McClelland, Maier & Neustadt, L.L.P.

(57) ABSTRACT

To provide a method for producing a perfluoro compound having hydroxyl groups, whereby agglomeration of a reduction reaction intermediate tends not to occur during a reduction reaction, and a perfluoro compound having —C(=O)OH can be used as a starting material.

Reducing $(A-C(=O)-Q-)_n R^{fn}$ in the presence of a metal hydride and an inorganic salt of lithium in an alcohol solvent to obtain $(B-CH(OH)-Q-)_{n-m}(A-C(=O)-Q-)_m R^{fn}$, wherein A is a hydroxyl group, a $C_{1-5}$ alkoxy group, a hydrogen atom, a $C_{1-5}$ alkyl group or the like, Q is a perfluoroalkylene group or the like, n is an integer of at least 1, m is an integer at least 0 and less than n, $R^{fn}$ is an n valent perfluoro saturated hydrocarbon group or the like, and B is a group depending on A wherein when A is a hydroxyl group, a $C_{1-5}$ alkoxy group or the like, B is a hydrogen atom, and when A is a hydrogen atom, a $C_{1-5}$ alkyl group or the like, B is the same group as A.

18 Claims, No Drawings

METHOD FOR PRODUCING A PERFLUORO COMPOUND HAVING HYDROXYL GROUPS

TECHNICAL FIELD

The present invention relates to a method for producing a perfluoro compound having hydroxyl groups.

BACKGROUND ART

As a method for obtaining a compound having hydroxyl groups by reducing an ester compound, for example, the following methods have been proposed.

(1) A method of reducing a compound of the following formula (I) to a compound of the following formula (II) by using a reaction mixture containing ethanol, sodium borohydride and an organic base (potassium tert-butoxide, sodium ethoxide or the like) (Patent Document 1):

$$ROC(=O)-CFW_1-O-R_f-CFW_2-C(=O)OR \quad (I)$$

$$HOCH_2-CFW_1-O-R_f-CFW_2-CH_2OH \quad (II)$$

wherein R is a $C_{1-5}$ alkyl group, $W_1$ and $W_2$ are a fluorine atom or a trifluoromethyl group, and $R_f$ is a perfluoroplyoxyalkylene group.

(2) A method of reducing 3-phenylpropionmethyl by using sodium borohydride and a metal salt in tetrahydropyran (Patent Document 2).

However, when the present inventors tried the method of (1), compounds of which all terminal ends are reduced could not be efficiently obtained due to the weak reducing force. Further, in a case where the method of (1) was applied to compounds having at least three —C(=O)OR, a problem was observed that reduction reaction intermediates agglomerated in the reduction reaction, and the reaction thereby stopped halfway.

In a case where the method of (2) is applied to perfluoro group-containing compounds having —C(=O)OR, there are problems such that since the solubility of the perfluoro group-containing compounds is low in tetrahydropyran, a heterogeneous reaction results, or time is required to accomplish the reaction.

Further, when the method of (2) was applied to perfluoro group-containing compounds having at least 2 —C(=O)OR, a problem was observed such that reduction reaction intermediates agglomerated in the reduction reaction, and the reaction stopped halfway.

PRIOR ART

Patent Documents

Patent Document 1: JP-A-2001-226482
Patent Document 2: JP-A-2008-001632

DISCLOSURE OF THE INVENTION

Object to be Accomplished by the Invention

It is an object of the present invention to provide a method for efficiently producing a desired compound (2), by carrying out a reduction reaction without agglomeration by using an easily available compound (1) having an A-C(=O)-terminal end group as a starting material.

Means to Accomplish the Object

A method for producing a perfluoro compound having hydroxyl groups, which comprises reducing a compound represented by the following formula (1) in the presence of a metal hydride and an inorganic salt of lithium in an alcohol solvent to obtain a compound represented by the following formula (2):

$$(A\text{-}C(=O)\text{-}Q\text{-})_n R^{fn} \quad (1)$$

$$(B\text{—}CH(OH)\text{-}Q\text{-})_{n-m}(A\text{-}C(=O)\text{-}Q\text{-})_m R^{fn} \quad (2)$$

wherein A is a hydroxyl group, a $C_{1-5}$ alkoxy group, a $C_{1-5}$ fluoroalkoxy group, a hydrogen atom, a $C_{1-5}$ alkyl group or a $C_{1-5}$ fluoroalkyl group, Q is a perfluoroalkylene group or a perfluoro alkylene group having an etheric oxygen atom between carbon-carbon atoms, n is an integer of at least 1, m is an integer at least 0 and less than n, $R^{fn}$ is an n valent perfluoro saturated hydrocarbon group or an n valent perfluoro saturated hydrocarbon group having an etheric oxygen atom between carbon-carbon atoms, and B is a group depending on A wherein when A is a hydroxyl group, a $C_{1-5}$ alkoxy group or a $C_{1-5}$ fluoroalkoxy group, B is a hydrogen atom, and when A is a hydrogen atom, a $C_{1-5}$ alkyl group or a $C_{1-5}$ fluoroalkyl group, B is the same group as A.

n is preferably an integer of from 1 to 4, m is an integer of from 0 to 3, and n>m is preferred.

n is preferably 3 or 4.

m is preferably 0.

The metal hydride is preferably sodium borohydride.

The compound represented by the formula (1) preferably has a molecular weight of at least 800.

The alcohol solvent is preferably a compound represented by the following formula (3):

$$R^3\text{—}OH \quad (3),$$

wherein $R^3$ is a $C_{1-6}$ alkyl group.

The compound represented by the formula (1) is preferably a compound represented by the following formula (11), and the compound represented by the formula (2) is preferably a compound represented by the following formula (21):

$$(A\text{-}C(=O)\text{-}Q\text{-})_n Y(\text{—}Z)_b \quad (11)$$

$$(B\text{—}CH(OH)\text{-}Q\text{-})_n Y(\text{—}Z)_b \quad (21)$$

wherein A is a hydroxyl group, a $C_{1-5}$ alkoxy group, a $C_{1-5}$ fluoroalkoxy group, a hydrogen atom, a $C_{1-5}$ alkyl group or a $C_{1-5}$ fluoroalkyl group, Q is a perfluoroalkylene group or a perfluoroalkylene group having an etheric oxygen atom between carbon-carbon atoms, n is an integer of 1 to 4, b is an integer of from 0 to 3, Y is a (n+b) valent perfluoro saturated hydrocarbon group or a (n+b) valent perfluoro saturated hydrocarbon group having an etheric oxygen atom between carbon-carbon atoms, and Z is a perfluoroalkyl group or a perfluoroalkyl group having an etheric oxygen atom between carbon-carbon atoms.

In the formulae (11) and (21), (n+b) is preferably 4, and Y is preferably a group represented by the following formula $(Y^4\text{–}1)$, $(Y^4\text{–}2)$, $(Y^4\text{–}3)$ or $(Y^4\text{–}4)$:

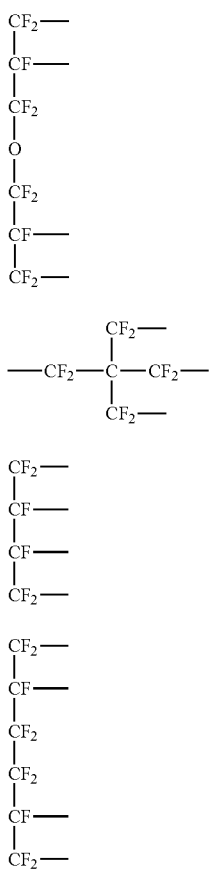

(Y⁴-1)

(Y⁴-2)

(Y⁴-3)

(Y⁴-4)

In the formulae (11) and (21), (n+b) is preferably 3, and Y is preferably a group represented by the following formula (Y³-1):

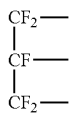

(Y³-1)

The amount of the metal hydride is from 1 to 2.5 times of the stoichiometric amount of the compound represented by the formula (1).

The amount of the inorganic salt of lithium is preferably from 10 to 50 mol % based on the amount of the metal hydride.

A mixture of the alcohol solvent and the metal hydride is preferably added to a mixture of the alcohol solvent, the compound represented by the formula (1) and the inorganic salt of lithium.

Effects of the Invention

According to the production method of the present invention, the compound (2) can be produced by efficiently carrying out a reduction reaction by using the easily available compound (1) having an A-C(=O)-group as a starting material without agglomeration.

MODE FOR CARRYING OUT THE INVENTION

The perfluoro compound in the present specification is a compound having a perfluoro group.

In the present specification, the compound represented by the formula (1) is referred to as the compound (1). Compounds represented by other formulae are also referred in the same manner.

Further, the group represented by the formula (Y⁴-1) is referred to as group (Y⁴-1). Groups represented by other formulae are also referred in the same manner.

The method of the present invention for producing a perfluoro compound having a hydroxyl group is a method of reducing the compound (1) in the presence of a metal hydride and an inorganic salt of lithium in an alcohol solvent to obtain the compound (2):

$$(A-C(=O)-Q-)_n R^{fn} \quad (1)$$

$$(B-CH(OH)-Q-)_{n-m}(A-C(=O)-Q-)_m R^{fn} \quad (2).$$

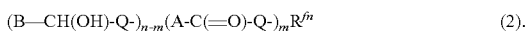

A is a hydroxyl group, a $C_{1-5}$ alkoxy group, a $C_{1-5}$ fluoroalkoxy group, a hydrogen atom, a $C_{1-5}$ alkyl group or a $C_{1-5}$ fluoroalkyl group.

The alkoxy group may, for example, be a methoxy group, an ethoxy group, a propoxy group, a butoxy group or an isopropoxy group.

The fluoroalkoxy group is an alkoxy group of which some of or all hydrogen atoms are substituted by fluorine atoms. The fluoroalkoxy group may, for example, be a trifluoromethoxy group, a pentafluoroethoxy group or a perfluoroisopropoxy group.

The alkyl group may, for example, be a methyl group, an ethyl group, a propyl group, a butyl group or an isopropyl group.

The fluoroalkyl group is an alkyl group of which some of or all hydrogen atoms are substituted by fluorine atoms. The fluoroalkyl group may, for example, be a trifluoromethyl group or a pentafluoroethyl group.

A is preferably an ethoxy group or an n-propoxy group, since by-products formed in the reduction reaction are alcohol compounds contained in an alcohol solvent used as a solvent in the present method, and its reduction reactivity is excellent.

Q is a perfluoroalkylene group or a perfluoroalkylene group having an etheric oxygen atom between carbon-carbon atoms. The perfluoroalkylene group is an alkylene group of which all hydrogen atoms are substituted by fluorine atoms. Q is preferably a group (Q1):

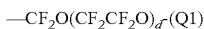

$$-CF_2O(CF_2CF_2O)_d- \quad (Q1)$$

wherein the group (Q1) bonds to $R^{fn}$ at the right end of the group (Q1).

d is an integer of from 1 to 200, preferably an integer of from 3 to 100, more preferably an integer of from 5 to 50.

In a case where n is at least 2, the groups (A) are preferably the same groups. The groups (Q) may be the same groups or different groups. Particularly, in a case where the group (Q) is the group (Q1), the group may have the same number of d or a different number of d. In the present invention, the group having a different unit number of d is considered to be the same group.

n is an integer of at least 1, preferably an integer of from 1 to 4, particularly preferably from 2 to 4, especially preferably 3 or 4. In the case of the compound having n of 3 or 4, the reaction proceeds remarkably preferably without the problem of agglomeration in the reaction system, as compared to known reactions.

m is an integer of at least 0 and less than n, preferably an integer of 0 to 3 and n>m, particularly preferably 0.

$R^{fn}$ is an n valent perfluoro saturated hydrocarbon group or an n valent perfluoro saturated hydrocarbon group having an etheric oxygen atom between carbon-carbon atoms. The n valent perfluoro saturated hydrocarbon group is an n valent saturated hydrocarbon group of which all hydrogen atoms are substituted by fluorine atoms.

$R^{fn}$ is preferably a group represented by the formula $Y(-Z)_b$. That is, $R^{fn}$ is preferably an n valent group wherein the number b of the group Z bond to the group Y. Here, b is an integer of from 0 to 3, preferably an integer of from 0 to 2, particularly preferably 0 or 1. $R^{fn}$ is particularly preferably the after-mentioned group (Y) (namely, a group represented by the formula $Y(-Z)_b$ when b is 0).

The compound (1) of which $R^{fn}$ is the group represented by the formula $Y(-Z)_b$ is the following compound (1A), and the compound (2) of which $R^{fn}$ is the formula $Y(-Z)_b$ is the following compound (2A):

$$(A\text{-}C(=O)\text{-}Q\text{-})_n Y(-Z)_b \qquad (1A)$$

$$(B-CH(OH)\text{-}Q\text{-})_{n-m}(A\text{-}C(=O)\text{-}Q\text{-})_m Y(-Z)_b \qquad (2A)$$

wherein Y is a (n+b) valent perfluoro saturated hydrocarbon group or a (n+b) valent perfluoro saturated hydrocarbon group having an etheric oxygen atom between a carbon-carbon bond. The (n+b) valent perfluoro saturated hydrocarbon group is a (n+b) valent saturated hydrocarbon group of which all hydrogen atoms are substituted by fluorine atoms.

In a case where Y has an etheric oxygen atom, the number of etheric oxygen atoms is preferably from 1 to 3. Since the etheric oxygen atom is an oxygen atom between carbon-carbon atoms, the etheric oxygen atom is not present on the terminal end of Y which bonds to Q or Z. Further, in a case where at least 2 etheric oxygen atoms are present in Y, at least two carbon atoms are preferably present between the respective two oxygen atoms. That is, it is preferred that Y does not have a $-OCF_2O-$structure, and it is preferred that the compound does not have a $-OCF_2O-$structure. Thereby, it is preferred that the $-OCF_2O-$structure is not present on the terminal end part which bonds to Q or Z. In the case of the compound having no $-OCF_2O-$structure, the chemical stability is remarkably improved, the reaction can be easily carried out, and formed products are stable.

Y is preferably one of groups $(Y^4-1)$ to $(Y^4-4)$ or a group $(Y^3-1)$.

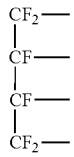
(Y⁴-1)

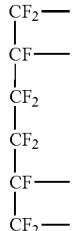
(Y⁴-2)

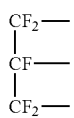
(Y⁴-3)

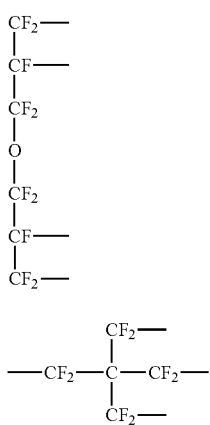
(Y⁴-4)

(Y³-1)

Z is a perfluoroalkyl group or a perfluoroalkyl group having an etheric oxygen atom between a carbon-carbon bond. The perfluoroalkyl group is an alkyl group of which all hydrogen atoms are substituted by fluorine atoms. Z is a group which does not change before and after the reaction.

In a case where plural Z are present in one molecule, they may be the same groups or different groups.

Z is preferably a group (Z1):

$$CF_3(CF_2)_sO(CF_2CF_2O)_g- \qquad (Z1).$$

s is an integer of from 0 to 19, preferably an integer of from 0 to 15, more preferably an integer of from 0 to 5.

g is an integer of from 3 to 200, preferably an integer of from 3 to 100, more preferably an integer of from 3 to 70, particularly preferably an integer of from 5 to 50.

What the group (Z1) is the same group means that the number of s is the same, and the number of g may be the same or different. The groups (Z1) are preferably the same group.

The group (Z1) is preferably a group (Z11), a group (Z12) or a group (Z13):

$$CF_3O(CF_2CF_2O)_g- \qquad (Z11)$$

$$CF_3(CF_2)_2O(CF_2CF_2O)_g- \qquad (Z12)$$

$$CF_3(CF_2)_5O(CF_2CF_2O)_g- \qquad (Z13).$$

B is a group which depends on A, and when A is a leaving group, B is a hydrogen atom, and when A is not a leaving group, B does not change. That is, when A is a leaving group selected from the group consisting of a hydroxyl group, a $C_{1-5}$ alkoxy group and a $C_{1-5}$ fluoroalkoxy group, B is a hydrogen atom, and when A is a non-leaving group selected from the group consisting of a hydrogen atom, a $C_{1-5}$ alkyl group and a $C_{1-5}$ fluoroalkyl group, B is the same group as A.

The compound (1) of which A is a leaving group is represented by the following compound (1B), and such a compound can be converted to the compound (2B):

$$(A^1\text{-}C(=O)\text{-}Q\text{-})_n R^{fn} \qquad (1B)$$

$$(HO-CH_2\text{-}Q\text{-})_{n-m}(A^1\text{-}C(=O)\text{-}Q\text{-})_m R^{fn} \qquad (2B)$$

wherein $A^1$ is a hydroxyl group, a $C_{1-5}$ alkoxy group or a $C_{1-5}$ fluoroalkoxy group. Other groups are as defined above.

Further, the compound (1) of which A is a non-leaving group is represented by the following compound (1C), and such a compound can be converted to the compound (2C):

$$(A^2\text{-}C(=O)\text{-}Q\text{-})_n R^{fn} \quad (1C)$$

$$(HO\text{—}CHA^2\text{-}Q\text{-})_{n-m}(A^2\text{-}C(=O)\text{-}Q\text{-})_m R^{fn} \quad (2C)$$

wherein $A^2$ is a hydrogen atom, a $C_{1-5}$ alkyl group or a $C_{1-5}$ fluoroalkyl group. Other groups are as defined above.

The compound (1) is preferably a compound (11), more preferably a compound (D4) or a compound (D3):

$$(A\text{-}C(=O)\text{-}Q\text{-})_n Y(\text{—}Z)_b \quad (11)$$

$$\{R^1O\text{—}C(=O)\text{—}CF_2O(CF_2CF_2O)_d\text{—}\}_4 Y^4 \quad (D4)$$

$$\{R^1O\text{—}C(=O)\text{—}CF_2O(CF_2CF_2O)_d\text{—}\}_3 Y^3 \quad (D3)$$

wherein $R^1$ is an alkyl group, preferably an ethyl group or a propyl group.

The compound (2) is preferably a compound (21) formed from the compound (11), more preferably a compound (E4) formed from the compound (D4) or a compound (E3) formed from the compound (D3):

$$(B\text{—}CH(OH)\text{-}Q\text{-})_n Y(\text{—}Z)_b \quad (21)$$

$$\{HO\text{—}CH_2\text{—}CF_2O(CF_2CF_2O)_d\text{—}\}_4 Y^4 \quad (E4)$$

$$\{HO\text{—}CH_2\text{—}CF_2O(CF_2CF_2O)_d\text{—}\}_3 Y^3 \quad (E3).$$

The molecular weight (the weight average molecular weight, hereinafter referred to as Mw) of the compound (1) and the compound (2) is preferably higher than 800, more preferably from 1,000 to 100,000, further preferably from 1,000 to 10,000. Since the reaction condition in the production method of the present invention has a merit to prevent agglomeration, such a reaction is particularly advantageous for compounds having a molecular weight of at least 800.

Mw is measured by gel permeation chromatography (hereinafter referred to as GPC).

The compound (1) and the compound (2) may, respectively, be composed of at least two compounds. In a case where they are, respectively, composed of at least two compounds, respective compounds preferably have the same $R^{fn}$ and different d in the group (Q1). The average of d in the group (Q1) is preferably a positive number of from 3 to 100. The average of g in the group (Z1) is preferably a positive number of from 3 to 100.

In the reaction of the present invention, in a case where all groups are reduced, m in the compound (2) is 0. However, in a case where a part of groups is not reduced and remains, plural compounds (2) will be formed. For example, four types of the compounds (2) wherein m is 0, 1, 2 and 3 will be formed from the compound (1) in which n is 4. Three types of the compounds (2) wherein m is 0, 1 and 2 will be formed from the compound (1) in which n is 3. The desired product depends on the application of the compound (2). Further, the reduction rate (the reduction rate is the proportion of the total mols of the group (B—CH(OH)-Q-) in the formed compound (2) to the total mols of the group (A-C(=O)-Q-) in the compound (1)) is preferably at least 98 mol %, particularly preferably at least 99 mol %. In a case where the compound (2) is to be used as a lubricant for magnetic disks, the compound (2) in which m is 0 is preferably efficiently obtained, and the method of the present invention has an advantage for carrying out a reaction having a high reduction rate.

The compound (1) and the compound (2) preferably have no —OCF$_2$O-structure from the viewpoint of the chemical stability. The compound having no —OCF$_2$O-structure is a compound wherein the —OCF$_2$O-structure cannot be detected by conventional analysis methods (such as $^{19}$F-NMR).

The metal hydride may, for example, be sodium borohydride (NaBH$_4$), lithium borohydride (LiBH$_4$) or lithium aluminum hydride (LiAlH$_4$), and sodium borohydride is preferred from the viewpoint of the handling efficiency and the easiness of industrial scale up.

The amount of the metal hydride is preferably from 1 to 2.5 times of the stoichiometric amount, more preferably from 1.5 to 2.0 times of the stoichiometric amount. When the amount of the metal hydride is at least 1 time of the stoichiometric amount, the reduction reaction of the compound (1) sufficiently proceeds. When the amount of the metal hydride is less than 2.5 times of the stoichiometric amount, the reduction of an alcohol solvent can be suppressed. The stoichiometric amount is a stoichiometrically required amount of the metal hydride for reducing A-C(=O)-Q- in the reaction system.

In the production method of the present invention, an inorganic salt of lithium is used in combination with the metal hydride. The effect obtained by using the inorganic salt of lithium in combination is considered to be as follows.

(i) If the weight average molecular weight of the compound (1) exceeds 800, the compatibility of the reduction reaction intermediates of which a terminal end bonds to a metal to a solvent deteriorates. Therefore, there is a problem such that the reduction reaction intermediates agglomerate in the reduction reaction, and the reaction stopped halfway. In the present invention, when an inorganic salt of lithium is used in combination, the electrification at the terminal end of the reduction reaction intermediates is released, and the dissolution or suspension state of the reduction reaction intermediates in the reduction reaction can be maintained. As a result, the compound (1) can be avoided from being released from the metal hydride due to agglomeration or precipitation, and the reduction reaction can be easily accomplished.

(ii) In a case where the reduction reaction is carried out only by using a metal hydride, there is a problem such that the group (A-C(=O)-Q-) remains. Further, in a case where A is a hydrolyzable leaving group, there is a problem such that a compound having a formed group (HO—C(=O)-Q-) is formed. It is considered that in the reaction of the present invention in which a metal hydride coexists with an inorganic salt of lithium, sodium borohydride is converted to lithium borohydride in the reaction system. Since the reduction efficiency of lithium borohydride is high, the compound (2) can be efficiently obtained.

From the viewpoint of the easiness of removal after the reaction, the inorganic salt of lithium is preferably a lithium halide, more preferably lithium chloride (LiCl) or lithium bromide (LiBr).

The amount of the inorganic salt of lithium is preferably from 0.1 to 100 mol %, more preferably from 10 to 50 mol %, based on the amount of the metal hydride. When the amount of the inorganic salt of lithium is at least 0.1 mol %, sodium borohydride is converted into lithium borohydride in the reaction system, and the reduction reaction of groups wherein the reduction efficiency is insufficient only with sodium borohydride (such as carboxyl groups) can be carried out. When the amount of the inorganic salt of lithium is at most 100 mol %, the inorganic salt of lithium can be easily extracted and removed by washing with water after the termination of the reaction.

In the production method of the present invention, an alcohol solvent is used as a solvent. The alcohol solvent is excellent in the solubility of the compound (1) which is a starting material, the inorganic salt of lithium, the metal hydride, the compound (2) which is a product to be formed and reduction reaction intermediates and tends not to be reduced by the metal hydride.

The amount of the alcohol solvent to be used is preferably from 0.5 to 5 L (liter), more preferably from 1 to 2 L, per 1 kg mass of the compound (1).

On the other hand, as another solvent for dissolving the compound (1) and the compound (2), a fluorine type solvent or a chlorine type solvent may be mentioned. However, since the solubility of the metal hydride in the fluorine type solvent is low, a large amount of such a solvent is required. Most of other solvents tend to be affected by the metal hydride in many cases, and for example, the chlorine type solvent has a drawback such that a dechlorination reaction results. Further, if the reaction temperature is lowered in order to prevent such a reaction, the reaction temperature is required to be controlled at a temperature where the reduction reaction does not proceed. Therefore, such other solvents are not practical.

The alcohol solvent is preferably the following compound (3). Further, the alcohol solvent is preferably methanol, ethanol, isopropanol or isobutanol from the viewpoint of the solubility of the metal hydride, the inorganic salt of lithium and the compound (1), particularly preferably ethanol from the viewpoint of the stability of the metal hydride:

$$R^3\text{—OH} \tag{3}$$

wherein $R^3$ is a $C_{1-6}$ alkyl group.

Further, the amount of moisture is preferably maintained as low as possible in order to maintain the activity of a reducing agent to be high. Thus, a dehydrated alcohol solvent is preferably used. The amount of moisture in the alcohol solvent is preferably at most 50 ppm. Further, the amount of moisture in the entire reaction system is preferably at most 1,000 ppm.

In the production method of the present invention, a metal hydride is preferably added in a mixture of the alcohol solvent, the compound (1) and the inorganic salt of lithium in order to maintain the stability of the metal hydride. More preferably, a mixture of the metal hydride and the alcohol solvent is added in the mixture of the alcohol solvent, the compound represented by the formula (1) and the inorganic salt of lithium.

In the production method of the present invention, the compound (1) is preferably reduced under an inert gas atmosphere from the viewpoint of handling safety of hydrogen gas formed as a by-product in the reaction.

The inert gas may, for example, be nitrogen, argon or helium.

The temperature for reducing the compound (1) (hereinafter referred to as reaction temperature) is preferably at least 0° C. and at most the boiling point of the alcohol solvent, more preferably from 0 to 30° C., further preferably from 0 to 15° C. When the reaction temperature is at least 0° C., the reduction reaction sufficiently proceeds. When the reaction temperature is at most the boiling point of the alcohol solvent, the compound (1) is reduced, and the alcohol solvent tends not to be reduced.

The reaction time is preferably from 0.1 to 10 hours, more preferably from 0.1 to 5 hours.

After the termination of the reduction reaction, the compound (2) is preferably washed with diluted hydrochloric acid.

The compound (2) is useful as a lubricant for magnetic disks (such as hard disks), a surface modifier (such as a surface modifier for controlling a refractive index of substrates or a surface modifier for improving chemical resistance of substrates), a wire coating material, a repellent ink agent (such as a repellent ink agent for painting or a repellent ink agent for printing machine (such as inkjets)), an adhesive for semiconductor (such as an adhesive for read on chip tapes), a protective coat for semiconductors (such as a moisture proofing agent or a creeping up preventing agent for solder), an additive for a thin film used in optical fields (such as pellicle films), a lubricant for a reflection protecting film for displays, a reflection protecting film for resist, a surface activating agent (such as an additive for lowering surface tension of a paint, a leveling agent for a paint or a leveling agent for a polishing liquid), etc.

In a case where the compound (2) is used as a lubricant for magnetic disks, m in the compound (2) is preferably 0. In other applications, m may be at least 1. Further, another functional group may be introduced by chemical conversion by utilizing the reactivity of A-C(=O)— in the compound (2).

EXAMPLES

Now, the present invention will be described in further detail with reference to Examples. However, it should be understood that the present invention is by no means thereby restricted.

In Examples, tetramethylsilane is referred to as TMS, $CCl_2FCClF_2$ is referred to as R-113, dichloropentafluoropropane is referred to as R-225, $CClF_2CClFCF_2OCF_2CClF_2$ is referred to as CFE-419, and hexafluoroisopropyl alcohol is referred to as HFIP.

(GPC Analysis)

The number average molecular weight (hereinafter referred to as Mn) and Mw were measured under the following condition by GPC in accordance with the method described in JP-A-2001-208736, and Mw/Mn was obtained.

Mobile phase: a mixed solvent of R-225 (ASAHIKLIN AK-225SEC grade 1, manufactured by Asahi Glass Company, Limited) and HFIP (R-255/HFIP=99/1 in volume ratio).

Column for analysis: two PLgel MIXED-E columns (manufactured by Polymer Laboratories Ltd.) were connected in series.

Standard samples for measuring the molecular weight: four types of perfluoropolyethers having less than 1.1 of Mw/Mn and molecular weight of from 2,000 to 10,000 and one type of perfluoropolyether having at least 1.1 of Mw/Mn and a molecular weight of 1,300.

The mobile phase flow rate: 1.0 mL/min

Column temperature: 37° C.

Detector: an evaporation light scattering detector (NMR Analysis)

TMS was used as the standard material of $^1$H-NMR (300.4 MHz).

$CFCl_3$ was used as the standard material of $^{19}$F-NMR (282.7 MHz).

Unless otherwise specified, R-113 was used as a solvent.

(Composition Ratio of Products)

Composition ratio of respective compounds contained in a formed product was measured by NMR analysis and infrared absorption spectrum analysis. That is, in $^{19}$F-NMR analysis, the existence of —$CH_2OH$ and —$C(=O)OCH_2CH_3$ was quantitative analyzed by the peak ratio of −80.1 ppm and −77.5 ppm derived from the $CF_2$ group which is adjacent to the above groups. Further, the existence of —C(=O)$OCH_2CH_3$ was measured by measuring the existence of the absorption peak derived from a carbonyl group at 8.00 ppm in $^1$H-NMR analysis and 1,700 ppm in IR analysis.

Example 1

The reaction was carried out in the same manner as in Example 11 (Working Example) of WO2005/068534, except that the kind of a polyoxyethylene glycerol ether was changed. That is, a commercially available polyoxyethylene glycerol ether (SC-C1500, manufactured by SAKAMOTO YAKUHIN KOGYO CO., LTD.) was reacted with FCOCF($CF_3$)O$CF_2$CF($CF_3$)O($CF_2$)$_3$F to obtain a compound (A4-1) which is liquid at room temperature. As a result of analysis, the average value of (d1+d2+d3+d4) of the compound (A4-1) was 27.5, $R^f$ was —CF($CF_3$)O$CF_2$CF($CF_3$)O$CF_2$$CF_2$$CF_3$, Mn was 2,900, and Mw/Mn was 1.14.

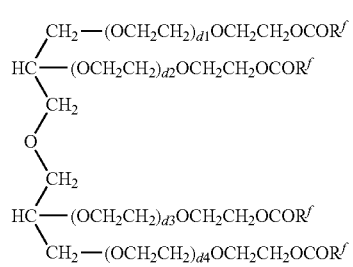

(A4-1)

$^1$H-NMR (solvent: $CDCl_3$) δ (ppm): 3.4 to 3.8, 4.5
$^{19}$F-NMR (solvent: $CDCl_3$) δ (ppm): −76.0 to −81.0, −81.0 to −82.0, −82.0 to −82.5, −82.5 to −85.0, −128.0 to −129.2, −131.1, −144.7

Example 2

The compound (A4-1) was fluorinated in the same manner as in Example 2-1 (Working Example) of WO2005/068534, except that a solvent R-113 was changed for CFE-419 to obtain a compound (B4-1). The compound (B4-1) was a compound wherein at least 99.9 mol % of hydrogen atoms in the compound (A4-1) was substituted by fluorine atoms.

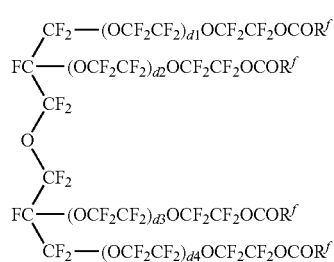

(B4-1)

$^1$H-NMR δ (ppm): 5.9 to 6.4
$^{19}$F-NMR δ (ppm): −55.8, −77.5 to −86.0, −88.2 to −92.0, −120.0 to −139.0, −142.0 to −146.0

Example 3

The compound (B4-1) was ester-decomposed to obtain a compound (C4-1) in the same manner as in Example 3 (Working Example) of WO2005/068534.

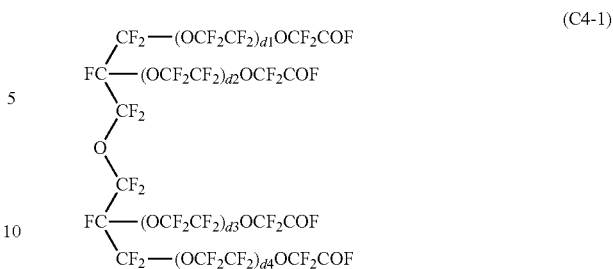

(C4-1)

Example 4

The compound (C4-1) was ester-reacted with ethanol to obtain a compound (D4-1) in the same manner as in Example 4 (Working Example) of WO2005/068534.

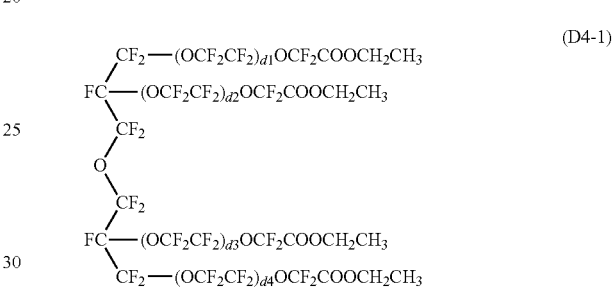

(D4-1)

$^1$H-NMR δ (ppm): 1.24, 3.68
$^{19}$F-NMR δ (ppm): −54.0, −77.5, −88.2 to −90.5, −135.0 to −139.0

Example 5

Nitrogen gas was preliminarily blown in an interior of a 5 L flask provided with a condenser which is cooled at 5° C. and a stirrer and connected to a pipe from a liquid feed pump. 12.5 g of commercially available lithium chloride was added in the flask at room temperature, and 1 L of dehydrated ethanol was added thereto. The mixture was stirred for 1 hour to completely dissolve lithium chloride, and 500 g of the compound (D4-1) obtained in Example 4 was added thereto.

Then, while stirring, the flask was cooled to 5° C. with ice. At the same time, a liquid feed pump and a liquid storage tank were provided in a cooling tank, and a solution prepared by diluting 40 g of sodium borohydride with 1 L of dehydrated ethanol was added in the liquid storage tank. Then, the full amount of the above solution was dropwise added in the flask by spending 2.5 hours. While dropping, the flask was maintained at 5° C., and the liquid storage tank was sealed with nitrogen gas. Then, the solution was heated to room temperature by spending 2 hours and then stirred for 12 hours. During the above heating and stirring, the formation of agglomerates in the reaction crude liquid was not observed.

Then, the reaction crude liquid was slowly added in a 5 L round-bottom flask in which 1 L of 0.02N hydrochloric acid aqueous solution, 0.5 L of R-225 and a stirrer chip were added. The mixture was stirred for 0.5 hours by using the stirrer, and then an organic layer was removed. The organic layer was washed with 1 L of 0.02N hydrochloric acid aqueous solution, and then the removed organic layer was washed with 1 L saturated salt solution. The recovered organic layer was concentrated by an evaporator to obtain 465 g of a colorless transparent viscous liquid at room temperature. As a result of analysis, the formed product was the compound (E4-1) wherein 99.9 mol % of ethyl ester groups in the compound (D4-1) was reduced, and the compound (E'4-1a) and the compound (E'4-1b) which have unreacted ethyl ester groups (hereinafter referred to as compound (E'4-1a) and compound (E'4-1b) are together referred to as compound (E'4-1)), and the compound (E"4-1a) and the compound (E"4-1b) which have —C(=O)OH (hereinafter the compound (E"4-1a) and the compound (E"4-1b) are together referred to as compound (E"4-1)) were not observed. A pattern of NMR spectrum of the formed product is shown below. Further, the composition ratio of respective compounds contained in the formed product is shown in Table 1.

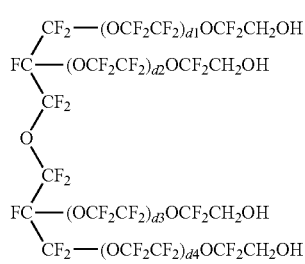
(E4-1)

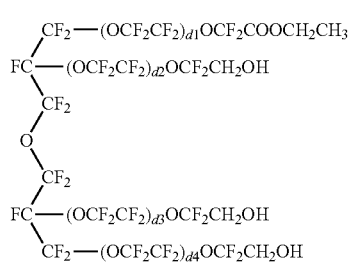
(E'4-1a)

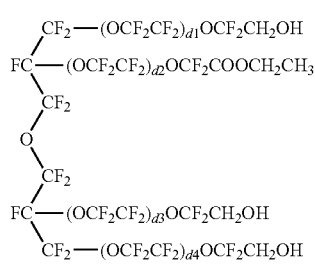
(E'4-1b)

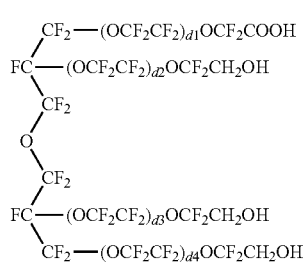
(E"4-1a)

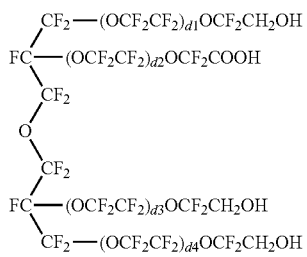
(E"4-1b)

$^1$H-NMR δ (ppm): 3.94
$^{19}$F-NMR δ (ppm): −54.0, −80.1, −88.2 to −90.5, −135.0 to −139.0

Example 6

Example 6-1

Comparative Example

The compound (E4-1) was produced in accordance with the method of Example 5 (Working Example) of WO2005/068534, except that the solvent was changed for ethanol.

Nitrogen was preliminarily blown in a 5 L flask provided with a condenser which is cooled at 5° C. and a stirrer and connected to a pipe from a liquid feed pump. 1 L of commercially available dehydrated ethanol and 40 g of sodium borohydride were added in a round-bottom flask at room temperature, and the mixture was stirred for 1 hour. Then, while stirring, the flask was cooled to 5° C. with ice. At the same time, a liquid feed pump and its liquid storage tank were provided in a cooling tank, and 500 g of the compound (D4-1) obtained in Example 4 was added in the liquid storage tank. Then, the full amount of the compound was dropwise added in a flask by spending 2.5 hours. Then, the mixture was heated to room temperature by spending 2 hours and stirred for 12 hours. Immediately after starting the dropwise addition of the compound (D4-1), many white agglomerations were formed, and after the termination of the dropwise addition, white agglomerations gradually gathered and precipitated at the bottom of the flask. After the termination of stirring for 12 hours, the separation state did not change.

The subsequent operations were carried out in the same manner as in Example 5 to obtain 445 g of a yellow transparent viscous liquid at room temperature. As a result of analysis, the formed product was one wherein 92 mol % of ethyl ester groups in the compound (D4-1) was reduced, mainly contained the compound (E4-1) and contained the compound (E'4-1) and the compound (E"4-1). A pattern of NMR spectral of the formed product is shown below. Further, the composition ratio of respective compounds contained in the formed product is shown in Table 1.

$^1$H-NMR δ (ppm): 1.24, 3.68, 3.94, 8.00
$^{19}$F-NMR δ (ppm): −54.0, −77.5, −80.1, −88.2 to −90.5, −135.0 to −139.0

TABLE 1

| | Composition ratio (mass %) | | | Recovery rate (mass %) | Formation of agglomerates |
|---|---|---|---|---|---|
| | E4-1 | E'4-1 | E"4-1 | | |
| Ex. 5 | 100 | 0 | 0 | 97 | None |
| Ex. 6-1 | 68 | 20 | 12 | 92 | Observed |
| Ex. 6-2 | 72 | 15 | 13 | 91 | Observed |

Example 6-2

Comparative Example

The compound (E4-1) was produced in accordance with the method described in Example 2 of JP-A-2001-226482.

That is, 1 L of dehydrated ethanol, 7.5 g of potassium tert-butyrate and 40 g of sodium borohydride were added in a 5 L reactor which is provided with a condenser cooled to 5° C. and a stirrer, wherein nitrogen was preliminarily blown its inside, and the mixture was stirred for 1 hour. Then, while stirring, the flask was cooled to 5° C. with ice. Then, 500 g of the compound (D4-1) obtained in Example 4 was dropwise added from a dropping funnel installed in the reactor by spending 1 hour. Then, the mixture was heated to room temperature by spending 2 hours and stirred for 12 hours. Immediately after the starting of the dropwise addition of the compound (D4-1), the formation of many white agglomerates was observed. Further, after the termination of dropwise addition, most of white agglomerates attached on a wall surface, and after the termination of stirring for 12 hours, the separation state did not change.

The subsequent operations were carried out in the same manner as in Example 5 to obtain 430 g of a yellow transparent viscous liquid at room temperature. As a result of analysis, the formed product is one wherein 91 mol % of ethyl ester groups in the compound (D4-1) was reduced, mainly contained the compound (E4-1) and contained the compound (E'4-1) and the compound (E''4-1). A pattern of NMR spectral of the formed product is shown below. Further, the composition ratio of respective compounds contained in the formed product is shown in Table 1.

$^1$H-NMR δ (ppm): 1.24, 3.68, 3.94, 8.00

$^{19}$F-NMR δ (ppm): −54.0, −77.5, −80.1, −88.2 to −90.5, −135.0 to −139.0

Example 7

The reaction was carried out in the same manner as in the method of Example 11 (Working Example) of WO2005/068534. That is, a commercial available polyoxyethylene glycerol ether (UNIOX G1200, manufactured by NOF Corporation) was reacted with FCOCF(CF$_3$)OCF$_2$CF(CF$_3$)O(CF$_2$)$_3$F to obtain a liquid compound (A3-1) at room temperature. As a result of analysis, the average value of (d1+d2+d3) of the compound (A3-1) was 20.5.

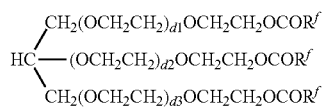
(A3-1)

Example 8

The compound (A3-1) was fluorinated in the same manner as in the method of Example 2-1 (Working Example) of WO2005/068534 to obtain a compound (B3-1), except that the solvent R-113 was changed for CFE-419. The compound (B3-1) was a compound wherein at least 99.9 mol % of hydrogen atoms in the compound (A3-1) was substituted by fluorine atoms.

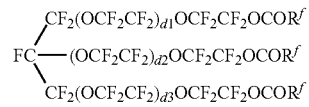
(B3-1)

Example 9

The compound (B3-1) was ester decomposed to obtain a compound (C3-1) in the same manner as in the method of Example 3 (Working Example) of WO2005/068534.

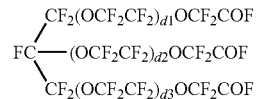
(C3-1)

Example 10

The compound (C3-1) was subjected to an esterification reaction by reacting with ethanol in accordance with the method described in Example 4 (Working Example) of WO2005/068534 to obtain a compound (D3-1).

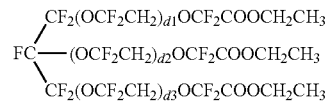
(D3-1)

Example 11

The same reaction was carried out as in Example 5 to obtain 455 g of a colorless transparent viscous liquid, except that instead of 500 g of the compound (D4-1), 500 g of the compound (D3-1) obtained in Example 10 was used. As a result of analysis, the formed product was a compound (E3-1) wherein 99.9 mol % of ethyl ester groups in the compound (D3-1) was reduced, and a compound (E'3-1a) and a compound (E'3-1b) which have unreacted ethyl ester groups (hereinafter, the compound (E'3-1a) and the compound (E'3-1b) are together referred to as compound (E'3-1)) and a compound (E''3-1a) and compound (E''3-1b) which have a —C(=O)OH group (hereinafter, the compound (E''3-1a) and the compound (E''3-1b) are together referred to as compound (E''3-1)) were not measured. Further, during the reduction reaction, agglomerates were not formed in the reaction crude liquid. The composition ratio of respective compounds contained in the formed product is shown in Table 2.

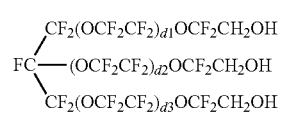
(E3-1)

-continued

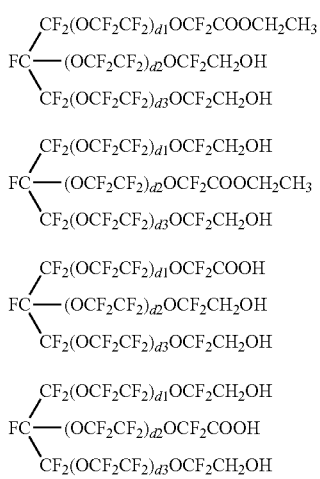

Example 12

Example 12-1

Comparative Example

The same reaction was carried out as in Example 6-1 to obtain 423 g of a yellow transparent viscous liquid at room temperature, except that instead of 500 g of the compound (D4-1), 500 g of the compound (D3-1) obtained in Example 10 was used. Immediately after starting the dropwise addition of the compound (D3-1), the formation of many white agglomerates was observed. After the termination of the dropwise addition, the agglomerates gradually gathered and precipitated at the bottom of the flask. After 6 hours from the termination of the reaction, the precipitate became one viscous chunk, and a stirrer could not be rotated.

As a result of analysis, the formed product was one wherein 92.1 mol % of ethyl ester groups in the compound (D3-1) was reduced, which mainly contained the compound (E3-1) and contained the compound (E'3-1) and a compound (E"3-1). The composition ratio of respective compounds contained in the formed product is shown in Table 2.

Example 12-2

Comparative Example

The same reaction as in Example 6-2 was carried out except that instead of 500 g of the compound (D4-1), 500 g of the compound (D3-1) obtained in Example 10 was used to obtain 410 g of a yellow transparent viscous liquid at room temperature. The formation of many white agglomerates were observed immediately after starting the dropwise addition of the compound (D3-1). After the termination of the dropwise addition, most of white agglomerates attached on a wall surface, and its state did not change after 12 hours from the termination of the reaction.

As a result of analysis, the formed product is one wherein 90.0 mol % of ethyl ester groups in the compound (D3-1) was reduced, which mainly contained the compound (E3-1) and contained the compound (E'3-1) and a compound (E"3-1). The composition ratio of respective compounds contained in the formed product is shown in Table 2.

TABLE 2

| | Composition ratio (mass %) | | | Recovery rate (mass %) | Formation of agglomerates |
|---|---|---|---|---|---|
| | E3-1 | E'3-1 | E"3-1 | | |
| Ex. 11 | 100 | 0 | 0 | 95 | None |
| Ex. 12-1 | 76 | 15 | 9 | 89 | Observed |
| Ex. 12-2 | 72 | 15 | 13 | 90 | Observed |

INDUSTRIAL APPLICABILITY

The perfluoro compound having hydroxyl groups obtained by the production method of the present invention is useful as a lubricant for magnetic disks.

The entire disclosure of Japanese Patent Application No. 2008-230708 filed on Sep. 9, 2008 including specification, claims, drawings and summary is incorporated herein by reference in its entirety.

What is claimed is:

1. A method for producing a perfluoro compound having hydroxyl groups, which comprises reducing a compound represented by the following formula (1) in the presence of a metal hydride and an inorganic salt of lithium in an alcohol solvent to obtain a compound represented by the following formula (2):

$$(A\text{-}C(=O)\text{-}Q\text{-})_n R^{fn} \tag{1}$$

$$(B\text{—}CH(OH)\text{-}Q\text{-})_{n-m}(A\text{-}C(=O)\text{-}Q\text{-})_m R^{fn} \tag{2}$$

wherein A is a hydroxyl group, a $C_{1\text{-}5}$ alkoxy group, a $C_{1\text{-}5}$ fluoroalkoxy group, a hydrogen atom, a $C_{1\text{-}5}$ alkyl group or a $C_{1\text{-}5}$ fluoroalkyl group, Q is a perfluoroalkylene group or a perfluoro alkylene group having an etheric oxygen atom between carbon-carbon atoms, n is an integer of at least 1, m is an integer at least 0 and less than n, $R^{fn}$ is an n valent perfluoro saturated hydrocarbon group or an n valent perfluoro saturated hydrocarbon group having an etheric oxygen atom between carbon-carbon atoms, and B is a group depending on A wherein when A is a hydroxyl group, a $C_{1\text{-}5}$ alkoxy group or a $C_{1\text{-}5}$ fluoroalkoxy group, B is a hydrogen atom, and when A is a hydrogen atom, a $C_{1\text{-}5}$ alkyl group or a $C_{1\text{-}5}$ fluoroalkyl group, B is the same group as A.

2. The method according to claim 1, wherein n is an integer of from 1 to 4, m is an integer of from 0 to 3, and n>m.

3. The method according to claim 1, wherein n is 3 or 4, and m is 0.

4. The method according to any one of claims 1 to 3, wherein the metal hydride is sodium borohydride.

5. The method according to claim 1, wherein the compound represented by the formula (1) has a molecular weight of at least 800.

6. The method according to claim 1, wherein the alcohol solvent is a compound represented by the following formula (3):

$$R^3\text{—}OH \tag{3}$$

wherein $R^3$ is a $C_{1\text{-}6}$ alkyl group.

7. The method according to claim 1, wherein the compound represented by the formula (1) is a compound represented by the following formula (11), and the compound represented by the formula (2) is a compound represented by the following formula (21):

$$(A\text{-}C(=O)\text{-}Q\text{-})_n Y(-Z)_b \quad (11)$$

$$(B\text{--}CH(OH)\text{-}Q\text{-})_n Y(-Z)_b \quad (21)$$

wherein A is a hydroxyl group, a $C_{1-5}$ alkoxy group, a $C_{1-5}$ fluoroalkoxy group, a hydrogen atom, a $C_{1-5}$ alkyl group or a $C_{1-5}$ fluoroalkyl group, Q is a perfluoroalkylene group or a perfluoroalkylene group having an etheric oxygen atom between carbon-carbon atoms, n is an integer of 1 to 4, b is an integer of from 0 to 3, Y is a (n+b) valent perfluoro saturated hydrocarbon group or a (n+b) valent perfluoro saturated hydrocarbon group having an etheric oxygen atom between carbon-carbon atoms, and Z is a perfluoroalkyl group or a perfluoroalkyl group having an etheric oxygen atom between carbon-carbon atoms.

8. The method according to claim 7, wherein (n+b) is 4, and Y is a group represented by the following formula ($Y^4$-1), ($Y^4$-2), ($Y^4$-3) or ($Y^4$-4):

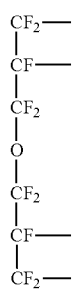
($Y^4$-1)

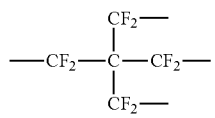
($Y^4$-2)

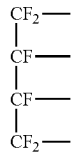
($Y^4$-3)

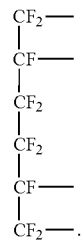
($Y^4$-4)

9. The method according to claim 7, wherein (n+b) is 3, and Y is a group represented by ($Y^3$-1):

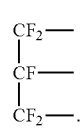
($Y^3$-1)

10. The method according to claim 1, wherein the amount of the metal hydride is from 1 to 2.5 times of the stoichiometric amount of the compound represented by the formula (1).

11. The method according to claim 1, wherein the amount of the inorganic salt of lithium is from 10 to 50 mol % based on the amount of the metal hydride.

12. The method according to claim 1, wherein a mixture of the alcohol solvent and the metal hydride is added to a mixture of the alcohol solvent, the compound represented by the formula (1) and the inorganic salt of lithium.

13. The method according to claim 1, wherein n is 3 or 4.

14. The method according to claim 1, wherein neither the compound represented by formula (1) nor the compound represented by formula (2) has an —$OCF_2O$— structure.

15. The method according to claim 1, wherein amount of the inorganic salt of lithium is from 0.1 to 100 mol %, based on the amount of the metal hydride.

16. The method according to claim 1, wherein amount of the inorganic salt of lithium is from 10 to 50 mol %, based on the amount of the metal hydride.

17. The method according to claim 1, wherein the alcohol solvent has a moisture content of at most 50 ppm.

18. The method according to claim 1, which is carried out in a reaction system having a moisture content of at most 1,000 ppm.

* * * * *